United States Patent [19]

Shalitin

[11] Patent Number: 4,877,867

[45] Date of Patent: Oct. 31, 1989

[54] ANTIBODIES FOR THE DETECTION OF MAMMALIAN RAS GENE PRODUCTS, METHOD OF PREPARING AND METHOD OF USING SAME

[76] Inventor: Channa Shalitin, 70 Pinsker Str., Haifa, Israel

[21] Appl. No.: 144,493

[22] Filed: Jan. 15, 1988

Related U.S. Application Data

[63] Continuation-in-part of Ser. No. 753,963, Jul. 11, 1985, Pat. No. 4,767,714.

[30] Foreign Application Priority Data

Jul. 19, 1984 [IL]  Israel ........................................ 72452

[51] Int. Cl.⁴ ............................ C07K 3/00; C07K 3/02
[52] U.S. Cl. ..................................... 530/387; 436/536; 436/543; 436/547; 530/350; 530/389
[58] Field of Search ........................ 530/387, 389, 350; 436/536, 543, 547

[56] References Cited

U.S. PATENT DOCUMENTS 3,867,255  2/1975  Newell et al. .
3,960,659  6/1976  Fazakerley .
3,996,104  12/1976  Gunilla et al. .

OTHER PUBLICATIONS

Papageorge et al.–Chem. Abst., vol. 100 (1984), p. 62,779c.
Carney et al.–Chem. Abst., vol. 104 (1986), p. 166,570b.
Temeles et al.–Chem. Abst., vol. 102 (1985), p. 144,911w.
Gulloev et al.–Chem. Abst., vol. 94 (1981), No. 61282f.

*Primary Examiner*—Sam Rosen
*Attorney, Agent, or Firm*—Browdy and Neimark

[57] ABSTRACT

Antibodies which are specific in their binding properties toward mammalian ras gene products are described. The antibodies are obtained from p20 polypeptide extracted from chromatin characterized by a molecular weight in the range of 16,000 to 21,000 daltons and the following amino acid composition: aspartic+glutamic acids in the range of 21.8–25.5 mole %; lysine+arginine in the range of 13.5–21.4 mole % and a ratio of lysine to arginine in the range of 2.31–3.1. The p20 polypeptide specifically reacts with the polyclonal anti-p20 antibodies. The antibodies are immunoreactive with yeast p20 polypeptide and with native p21 ras related proteins expressed in tumor cells. Accordingly, the antibodies are suggested to serve as additional probes for assessing the expression of ras gene related proteins in human malignancy.

11 Claims, 2 Drawing Sheets

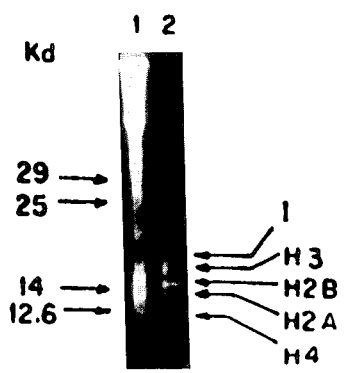
FIG.1A  FIG.1B
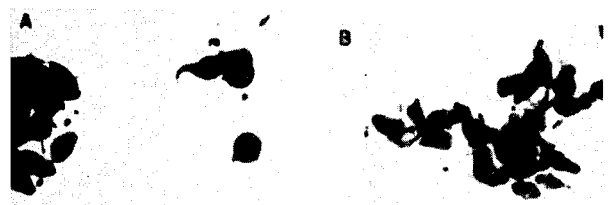
FIG.2A  FIG.2B
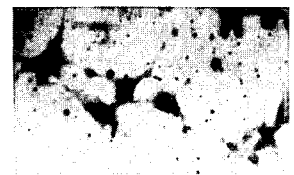
FIG.2C

ANTIBODIES FOR THE DETECTION OF MAMMALIAN RAS GENE PRODUCTS, METHOD OF PREPARING AND METHOD OF USING SAME

This patent application is a continuation in part to the parent patent application Ser. No. 753,963 filed on July 11, 1985 now matured into U.S. Pat. No. 4,767,714.

The present invention relates to antibodies which are specific in their binding properties towards mammalian ras gene products.

In our parent patent application a method was described for the preparation of pure chromatin from yeast and isolation of p20 polypeptide thereof.

BACKGROUND OF THE INVENTION

One of the families of cellular oncogenes most commonly implicated in a wide variety of malignancies is the c-ras family. Overexpression of the c-ras gene has been observed in a human colon cell line (McCoy et al, Nature London 32, 79–81, 1983). Thus, both quantitative and qualitative changes affecting the level of expression of the c-ras genes may be considered to be associated with tumorigenesis.

Genes related to ras have been identified in lower organisms such as *Saccharomyces cerevisiae*, Drosophila and Dictyostelium. The presence of ras genes in nocancerous cells and in evolutionarily diverse organisms suggested that these genes have fundamental importance in cellular physiology. *Saccharomyces cerevisiae* contains six genes whose protein products share homology with the mammalian ras oncogene products. Yeast ras-related protein YP2 shares about 40% homology in the amino terminal 160 amino acids with mammalian ras proteins (Gallwitz et al., Nature London 306, 704–7, 1983). Furthermore, RAS1 and RAS2 yeast genes are 62% homologous with mammalian ras in the same region (Dahr et al, Nucl. Acids Res. 12, 3611–18, 1984 and Powers et al Cell 36, 607–12, 1984).

Also, two rho genes with significant homology to the ras oncogene have been isolated recently (Maduale et al, Proc. Natl. Acad. Sci. 84, 779–89, 1987). Another gene, SEC4 was recently shown to share 32% homology with ras proteins (Salminen et al. Cell 49, 527–38, 1987).

A description of the ras gene family, on which the present invention does apply is given in a recent review article (M. Barbacid, Ann. Rev. Biochem, Vol 56, 779–827, 1987). These c-ras genes are expressed at low level in most cells. Cross reactive antisera have detected low levels of p21 proteins in almost all cell lines examined (Langbeheim et al, Virology 106, 292–300, 1980). However, the transcriptional activity of ras oncogenes (Ha-ras, Ki-ras) was found to be greater in malignant than in normal tissues. This included renal cell carcinoma, ovarian and colon adenocarcinoma, carcinoma of the lung and the breast and acute myeloid leukaemia (Slamon et al. Science 224, 256–62, 1984).

In a previous abstract paper (Baratal and Shalitin, Proc. Amer. Assoc. for cancer Res. 27, 427, 1986) we described the generation of anti-YP2 rabbit polyclonal antibodies against native yeast ras related protein YP2. These antibodies were shown to immunoreact with mammalian p21 protein.

As known all members of the ras gene family encode closely related proteins having a molecular weight of about 21,000 daltons, which have been designated p21. The level of p21 expressions is similar in many different human tumor cell lines, independent of whether the cell line contains an activated ras gene detectable by transfection (Der and Cooper, 1983, Cell 32, 201–208).

Human neoplasia could be determined by histological examination of by DNA-mediated transfection assay with mouse NIH 3T3 fibroblasts. Foci of transformed cells are scored after 21 days and only 10% of the urinary tract tumors yielded foci in this test (Fujita et al., 1984, Nature 309, 464–466).

Nucleotide sequence analysis of the $ras^H$ transforming gene of human bladder carcinoma cells indicated that the transforming activity of this gene is a consequence of a point mutation altering amino acid 12 of p21 from glycine to valine (Tabine et al. 1982, Nature 300. 143–149; Reddy et al., 1982, Nature 300, 149–152; Capon et al., 1983, Nature 302, 33–37; Reddy, 1983, Science 220, 1061–1063.)

The altered p21 protein displayed abnormal electrophoretic mobility on SDS-polyacrylamide gels. Furthermore, proteins encoded by $ras^K$ genes previously activated in four human lung and colon carcinoma cell lines, also displayed abnormal electrophoretic mobilities (Der and Cooper, 1983, Cell 32, 201–208). It further appeared that different mutations could activate the same $rsa^K$ gene in different individual neoplasms (Der and Cooper, 1983, Cell 32, 201–208).

Detection of human cancer cells by molecular diagnosis of restriction sites is tiresome. An easy way of diagnosis is by electrophoretic separation of proteins derived from cancer cell extracts on SDS - polyacrylamide gels, (Western blots) and staining by specific antibodies. Carcinoma cells which express ras proteins with identical electrophoretic mobility to those of normal human cells, might express the protein at a level 3-5 fold higher than primary fibroblasts or epithelial cultures (Der and Cooper, 1983, Cell 32, 201–208).

It is an object of the present invention to provide anti p20 antibodies which are very specific in their binding properties towards human p21 Ha-ras and Ki-ras gene products using immunoprecipitation, immunoblotting and indirect immunofluorescence.

BRIEF DESCRIPTION OF THE INVENTION

The invention relates to antibodies specific in their binding properties towards human p21 Ha-ras and Ki-ras gene products, said antibodies being obtained from p20polypeptide having a molecular weight in the range of 16,000 to 21,000 daltons and amino acid composition as follows: asparatic+glutamic acids in the range of 13.5–21.4 mole % and a ratio of lysine to arginine in the range of 2.31–3.1.

The polypeptides found to be useful for the present invention are defined as p20 and include the p20polypeptide obtained from pure chromatin as described in the parent patent application Ser .No. 753,963, as well as other polypeptides prepared from other sources, either in the form of p20 or p16 to p21 which are degraded or modified forms of the p20 polypeptide. They are characterized by their molecular weight in the range of 16,000 to 21,000 daltons as well as their amino acid composition as given above.

BRIEF DESCRIPTION OF THE DRAWINGS

FIG. 1 is a Western blot of p20 isolated from yeast chromatin,

FIG. 2 is a picture of the immunofluorescence of fixed culture cells stained with pAb to p20 ras-related protein.

MATERIALS AND METHODS

Figure 3:
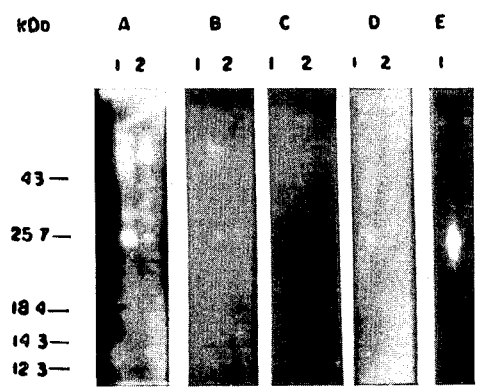
FIG. 3 illustrates the Western blot analysis of cytoplasmic antigens with polyclonal antibodies.

Antibodies:

p20 protein was isolated from yeast chromatin by micrococcal nuclease digestion and purified by sucrose gradient centrifugation. Sucrose gradient fractions containing the p20 polypeptide were lyophilized and resuspended in 50 µl of a buffer containing 0.35M NaCl, 10 mM Tris-HCl pH 8.0, 1 mM EDTA, 1 mM DTT, and two protease inhibitors, 1 mM PMSF and 1 mM NaHSO$_3$. After 30 min on ice, the mixture was centrifuged at 12,000 rpm for 10 min.

Rabbits were immunized using 40 µg portions of salt extracted p20 polypeptide emusified in complete Freund's adjuvant (Difco Lab, Detroit, Michigan), supplemented with 5 mg Mycobacterium tuberculosis cells, and injected intradermally into rabbits at multiple sites. The rabbits were given booster injections with 40 µg protein at 5 weeks after the first injection and bled 1-2 weeks later. Polyclonal antibodies were precipitated using an equal volume of 3.14 M ammonium sulfate. The precipitate was redissolved in phosphate buffered saline (PBS) pH 8.0 and dialyzed against several changes of PBS pH 8.0. The antibodies were then loaded onto a protein A-Sepharose CL-4B column (Sigma). The bound antibodies were eluted with 0.1M sodium citrate buffer pH 2.5, dialyzed against PBS (pH 7.4) at a concentration of 800 µg/mol IgG. The concentration of the antibodies was determined by the Bradford Method (Bio-Rad Laboratories. Richmond, Calif.). The purifity of the antibodies was demonstrated by analysis on 10% polyacrylamide SS gels in the presence of 2-mercaptoethanol. Anti-p21 pan-reactive mouse monoclonal Ab was purchased from Cetus Diagnostics, Emeryville, CA.

Slide preparation for Immunofluorescence:

Twenty five ul of a tumor cell suspension (5×10$^4$ cells/ml) were placed in each of the wells on plastic-coated multiwell slides (Hendley-Essex, Sussex, England). These slides were incubated at 37° C. in an atmosphere of 5% CO$_2$ for 48 hr. This process permits the antigenbearing cells to adhere to the glass and spread out. In this way, antigen distribution can subsequently be more readily determined. The slides were then washed twice with PBS, air dried, fixed in acetone for 10 min and stored at −20° C. The remaining steps were as described below.

Indirect Immunofluorescence:

Anti-p20 antibodies were diluted 10 fold and placed on the well of prepared slides which were then incubated for 1 hr at 37° C. After incubation, slides were washed twice for 5 min with PBS followed by a short immersion in distilled water. After complete drying, 1:20 diluted IgG (specific affinity purified goat anti--rabbit immunoglobulin) conjugated with fluorescein isothiocyanate (sigma, St. Louis, MO) were placed on the wells, and slides were again incubated for 1 hr at 37° C. Following the second incubation, the wash cycle was repeated, and the slides still wet, were then placed for 5 min in Evan's blue (0.005%). This step counterstains those portions of the cells which have no antigen and diminishes nonspecific autofluorescence. Finally, the slides were washed again, dried, covered with 50% glycerol, and examined using a Leitz Ortholux II microscope. Negative controls included normal rabbit serum incubated with the cells or secondary FITC conjugate with no primary antibody added.

Cell Lysates:

Cell lysis buffer contained 1% Triton X100, 0.14M NaCl, 0.025M Tris-HCl pH 7.5 and two protease inhibitors −2 mM phenylmethylsulfonyl fluoride (PMSF) and 1 mg/ml aprotinin (Sigma, St. Louis, MO.).

Immunoblotting:

Lysates were cleared by centrifugation in a minifuge at 12000 rpm for 15 min. The supernatant fluid was resolved by NaDodSO4/polyacrylamide gel electrophoresis on 15% polyacrylamide minigels without boiling in sample buffer. The proteins were electroblotted from the gel onto nitrocellulose paper. Blotted protein standards were separated from the rest of the nitrocellulose paper and stained in a 0.01% amidoblack solution. Free sites on the nitrocellulose filter were blocked by incubation for 1 hr at room temperature and overnight at 4° C. in a buffer containing 10 mM Hepes (pH 8.0) and 5% (wt/vol) nonfat dry milk (Cadbury's Marvel). Anti-p20 antibodies or normal rabbit serum (Sigma, St. Louis, MO.) (1:100 dilution) were added to a buffer containing 140 mM NaCl, 25 mM Tris-HCl (pH 7.5) and 1% bovine serum albumin, and the binding of antibody allowed to proceed for 16 hr at room temperature. Filters were washed five times with the buffer containing 140 mM NaCl, 25 mM Tris-Hcl (pH 7.5) and 1% BSA. Finally, the filters were incubated for 1 hr with $^{125}$-I-labeled protein A. After incubation, the filters were washed five times with NaCl/Tris buffer, dried and autoradiographed at −70° C. with Fuji RX film plus intensifying screens.

Binding of [α$^{32}$-P]-GTP:

The filters were incubated for 1 hr at room temperature in binding buffer (10 mM Hepes, pH 8.0, 50 mM NaCl, 10 mM MgCl$_2$, 0.1 mM EDTA, 1 mM dithiothreitol, 0.25% nonfat dry milk and 10 µCi [α-$^{32}$-P]GTP (3000 Ci/mmol, Amersham, U.K.). The filters were washed in two changes of binding buffer over a period of 2 hr and then exposed to Fuji XR film for 18 hr.

Cell labeling and Immunoprecipitation:

Cultures were labeled for 18 hr in small flasks containing 5 methionine-free medium and 200 µCi/ml [$^{35}$S] methionine (1205 Ci/mmol, Amersham, U.K.). Cell extracts were prepared by lysing 2.5×10$^7$ cells per ml in lysis buffer as described above containing 0.1% SDS and 0.5% Na deoxycholate. After 30 min on ice, the extracts were clarified by centrifugation in a minifuge for 15 min 12,000 g at 4° C. and a volume of extract containing 2-4 ×10$^7$ cpm of acid-insoluble radioactivity was added to 30 µl PBS pH 7.4 containing affinity purified polyclonal antibodies or normal rabbit IgG as control at a final concentration of 80 µġ/mol. After incubation of 1 hr at 4° C., immunoprecipitates were precipitated by the addition of 50-100 µl of a 50% slurry of protein A-Sepharose pretreated consecutively with 10 mg/ml BSA in PBS and cold mouse fibroblast lysate to prevent nonspecific binding of radiolabeled proteins. When mouse monoclonal antibody was used, protein A-Sepharose was precoated with rabbit anti-mouse IgG (Sigma, St. Louis, MO.). The complexes were kept overnight at 4° C. Immune complexes were washed three times with 100 µl lysing buffer at 4° C., after which the immunoprecipitates were eluted by heating the Sepharose beads for 10 min at 90° C. in 20 µl Laemmli double concentrated sample buffer containing 2-mercaptoethanol. After centrifugation for 15 min 12,000 g at 4° C., the supernatant was analyzed by electrophoresis in 15% SDS-polyacrylamide gels followed by fluorography using Amplify (Amersham) and autoradiography.

Results

Specificity of rabbit anti-p20 antibodies.

To establish the specificity of rabbit anti-p20 antibodies, immunological staining of proteins isolated from yeast chromatin by sucrose gradients and by SDS-polyacrylamide gel electrophoresis (Western blots) was performed, as illustrated in FIG. 1. The p20 specifically reacted with the polyclonal anti-p20 antibodies. No reaction was obtained when non-immune antisera was used. FIG. 1A left—demonstrates the sucrose gradient fraction No. 2 collected from the top of the gradient (lane 1), and yeast histones prepared according to the procedure of sommer (lane 2), (Coomassie stained). The molecular sizes are given in daltons $\times 10^3$. Right—Electrophoretic transfer immunoblot of identical lanes as in the Coomassie stained gel, showing immunoreaction of p20 polypeptides. After incubation with antibody, the nitrocellulose paper was incubated with horse-radish peroxidase protein A conjugate (Sigma). The nitrocellulose paper was washed and subsequent color development was done with hydrogen peroxide and 3,4,3',4' tetraaminobiphenyl hydrochloride.

Figure 4:
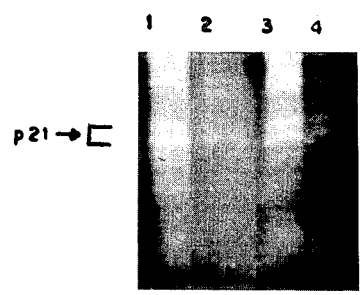
FIG. 4 illustrates the immunoprecipitation of p21 protein by anti-p20 rabbit polyclonal antibodies as compared with mouse monoclonal anti-p21 antibodies.

Specific determination of mammalian p21 ras proteins by anti-p20 antibodies is demonstrated in FIG. 4.

Indirect immunofluorescence using anti-p20 antibodies

Indirect immunofluorescent staining of human tumor cell lines using anti-p20 antibodies showed that 12 of 16 sarcoma and carcinoma cell lines were reactive with the antibodies as shown in the following Table 1.:

TABLE 1

Indirect immunofluorescent staining of human tumor cell lines.

| Cells | Type | IFA |
| --- | --- | --- |
| WLS | Liposarcoma | W |
| SAOS | Osteosarcoma | − |
| GOS | Osteosarcoma | + |
| VOS | Osteosarcoma | W |
| MCS | Chondrosarcoma | W |
| RLES | Sarcoma | + |
| SFLC | Sarcoma | + |
| EES | Ewing Sarcoma | + |
| KMS | Myxosarcoma | + |
| PRNS | Sarcoma | + |
| WSCS | Spindle Cell Sarcoma | + |
| A26674 | Carcinoma | − |
| SW 582 | Colon Carcinoma | + |
| MT 29 | Cervix Carcinoma | + |
| SW 480 | Colon Carcinoma | + |
| KNS | Normal skin | + |
| T24 | Bladder Carcinoma | + |

In Table 1 the staining pattern was as follows: w, weak; +, strong staining; −, no staining.

As shown in the above Table 1, EES cell line was found to strongly bind anti-p20 antibodies.

The immunofluorescence microscopy was used in order to examine the specificity of the anti-p20 antibodies to p21 in normal NIH-3T3 mouse fibroblasts as compared with NIH-3T3 cells transfected with human bladder carcinoma DNA (T24) and is illustrated in FIG. 2. The sample was prepared as follows: NIH-3T3 cells transfected with T24 human bladder carcinoma DNA [A and B] or NIH-3T3 mouse fibroblasts [C], were grown to 50% confluency on coverslips. Cells were gently fixed (3.5% formaldehyde) in PBS for 10 min at room temperature and stained with affinity purified pAb and processed for immunofluorescence (as described above under Methods).

Immunofluorescent pictures were taken on Agfapan (400 ASA) film with the same exposure time at a magnification of 320X. A significant fluorescent signal was obtained when anti-p20 IgG was used to stain T24 transfected cells as appears from FIG. 2A. Controls were also performed by incubating cells with normal rabbit IgG followed by the second antibody FITC conjugate, low levels of fluorescence were observed due to conspecific binding by this IgG. These results are presented in FIG. 2B. Staining of cells with second antibody FITC conjugate without the primary antibodies lack any fluorescence. Also, the untransfected NIH-3T3 cells showed little or no specific staining as appear from FIG. 2C. The localization of the antibodies to the plasma membrane (FIG. 2A) is in accord with previous results [Willingham et al, 1980 Cell 19, 1005–1014]. Thus our antibodies are capable of distinguishing aggressive from non-infiltrating cells on the basis of ras expression. Polyclonal anti-p20 antibodies react with human ras$^H$ p21s Polyclonal antibodies anti-p°, a yeast ras related protein, were used for immunoblotting with human ras$^H$ (FIG. 3). The sample was prepared as follows: Cytoplasmic extract of cells was prepared as described in experimental procedures. Cell fractions were electrophoresed on a 15% SDS-polyacrylamide gel. Western blots were incubated with anti-p20 antibodies [A]; or with anti-p20 antibodies blocked by 55 ug p20 polypeptide prior to incubation with the Western blot [B]; the blot was incubated without antibodies [C]; the blot was incubated with anti-p21 pan-reactive monoclonal antibody (Cetus Diagnostics Inc., Emeryville, CA; diluted 100 fold) followed by incubation with 2 $\mu$Ci $^{125}$I Sheep anti-mouse IgG [D]; the blot was preincubated with anti-p20 antibodies prior to incubation with [$\alpha$-$^{32}$p] GTP (E).

Cytoplasmic extract in each lane was as follows:

(35 $\mu$g protein/slot). 1-3T3/NIH cells transfected with human bladder carcinoma DNA (T24). 2- 3T3/NIH cells.

The lower electrophoretic mobility of p21 encoded by activated ras$^H$ gene of T24 carcinoma is clearly observed in this Figure. The endogenous c-ras p12 is also immunoreactive with anti-p20 antibodies as can be seen in the control NIH-3T3 cells (FIG. 3A lane 2). The specificity of the immunoreaction was demonstrated by the blocking of the immunoreactivity of the antibodies by preincubation with the p20 peptide (FIG. 3B), or omitting the antibodies from the immunoblot (FIG. 2C).

Similar results were obtained when p21 pan-reactive mouse monoclonal antibody (prepared to a synthetic peptide residues 29 through 44- Cetus Diagnostics, Emryville, CA) was used (FIG. 3D). Anti-p20 antibodies at the concentration used under the experimental conditions did not block the GTP-binding activity of the human ras protein in-vitro (FIG. 3E).

Detection of p21 proteins by anti-p°antibodies using immunoprecipitation.

Ras p21 expression using anti-p20 antibodies was compared with anti-p21 pan-reactive (Cetus Diagnostics, Emeryville, CA) mouse monoclonal Ab using the immunoprecipitation technique. NIH-3T3 cells transfected with T24 human bladder carcinoma DNA were labeled with [$^{35}$S] methionine, immunoprecipitated with affinity purified anti-p20 IgG, or normal rabbit IgG and the precipitated proteins were analyzed by SDS-polyacrylamide gel electrophororesis. The same cell line was used for immunoprecipitation with anti-p21 mouse monoclonal antibody (Cetus Diagnostics, Emeryville, CA.). Normal mouse IgG served as control. The results are shown in FIG. 4. The sample was prepared as follows: Cultures of NIH-3T3 cells transfected with T24 human bladder carcinoma DNA were metabolically labeled overnight with [$^{35}$S] methionine (200 µCi/ml) in methionine-free medium. Extracts of whole cells were prepared as under Methods. Immunoprecipitation was done with anti-p20 IgG (80 µg/ml) [lane 1], or with normal rabbit IgG (80 µg/ml) [lane 2]. With anti-p21 pan-reactive mouse monoclonal antibody (Cetus Diagnostics, Emeryville, CA., 3.3 µg/ml) [lane 3], or with normal mouse IgG (3.3 µg/ml) [lane 4]. The immunoprecipitates were analyzed by 15% SDS-polyacrylamide gel electrophoresis followed by fluorography and autoradiography. [$^{14}$C] methylated proteins molecular weight standards (Amersham) were coelectrophoresed. The positions of the p21 protein is indicated by the arrow. As compared with the proteins immunoprecipitated with normal rabbit IgG (FIG. 4, lane 2) anti-p20 IgG reacts strongly with human p21 from T24 transfected 3T3 cells (FIG. 4, lane 1). The p21 protein revealed by anti-p20 antibodies co-migrated with the p21 protein detected by anti-p21 pan-reactive monoclonal antibody. Ha-ras p21 is usually detected as a doublet species with the upper band corresponding to pro-p21 and the lower band corresponding to mature p21. When all the available p21 had been removed by exhaustive precipitation with either anti-p20 IgG or anti-p21 monoclonal antibody, no free p21 could then be precipitated by either anti-p20 IgG or anti-p21 monoclonal antibody in a second precipitation reaction. This is consistent with the same p21 protein being involved and not with distinct p21 proteins being precipitated by anti-p20 IgG on one hand and anti-p21 monoclonal antibody on the other.

It was found that antibodies are immunoreactive with p21 proteins resolved by NaDodSO$_4$ polyacrylamide gels without boiling in the sample buffer. The antibodies recognize normal as well as altered Ha-ras and Ki-ras gene products such as in SW480 colon carcinoma and T24 bladder carcinoma cell lines. In these cells the ras gene product was expressed at levels 2 to 4 fold greater than the level observed in non-transformed NIH-3T3 cells. The proteins reacting with the pAbs under the experimental conditions have been shown to bind alpha-$^{32}$p labeled GTP. However previously identified polyclonal and monoclonal antibodies were able to interfere with the GTP-binding function of p21.

Anti-p20 antibodies have been shown to immunostain carcinomas and sarcomas. Twelve of sixteen sarcoma and carcinoma cell lines were stained with anti-p20 pAbs. It is noteworthy that one human fibroblast cell line derived from normal skin was immunostained with anti-p20 antibodies. This is in accordance with previous observations of a 4 fold amplification of C-Ha-ras-1 during the lifespan of normal human diploid fibroblasts in-vitro.

Polyclonal antibodies generated to different peptide domains of ras proteins, detected proteins related to ras genes in 90% of tested tumors. However, these proteins were found in normal tissues examined, and there was no dramatic difference in p21 expression between cancer and homologous normal tissue except in one case.

In contrast to polyclonal and monoclonal antibodies described in the prior art which immunoreact with denatured p21 proteins only, the anti-p20 antibodies described herein are immunoreactive with nonfixed fresh frozen tissue sections and with native p21 ras related proteins expressed in tumor cells. Thus, these antibodies can serve as an additional tool to investigate the huge variations in clinical patterns in human cancers. They may be useful in the localization of ras determinants in primary and metastatic tumors. Anti-p20 antibodies which interact with native p21 ras-related proteins may be valuable for the identification and analysis of cellular macromolecules that interact with p21 which may be critical in understanding the function of p21 in malignant transformation.

I claim:

1. Antibodies specific in their binding properties towards nonfixed mammalian ras gene-expressed proteins, obtained using, as an immunogen, a p20 polypeptide derived from chromatin or the degraded p20 polypeptide having a molecular weight in the range of 16,000 to 20,000 and amino acid composition as follows: aspartic+glutamic acids in the range of 21.8–25.5 mole %; lysine + arginine in the range of 13.5–21.4 mole % and a ratio of lysine to arginine in the range of 2.31–3.1.

2. Antibodies according to claim 1 wherein said p20 polypeptide is obtained from chromatin.

3. Antibodies according to claim 2, wherein said chromatin is derived from *Saccharomyces cerevisiae.*

4. Antibodies according to claim 1, wherein said immunogen is a degraded p20 polypeptide.

5. Antibodies according to claim 1, which are obtained using yeast chromatin p20 polypeptide as said immunogen.

6. Anti-p20 antibodies according to claim 1, which are immunoreactive with normal as well as altered Ha-ras and Ki-ras gene-expressed proteins in SW480 colon carcinoma and in T24 bladder carcinoma cell lines.

7. A method for obtaining anti-p20 antibodies which are specific in their binding properties towards mammalian ras gene-expressed proteins wherein animals are immunized with portions of sodium chloride-extracted p20 polypeptide derived from chromatin or the degraded p20 polypeptide having a molecular weight in the range of 16,000 to 20,000 and amino acid composition as follows: aspartic +glutamic acids in the range of 21.8–25.5 mole %; lysine +arginine in the range of 13.5–21.4 mole % and a ratio of lysine to arginine in the range of 2.31–3.1 emulsified in complete Freund's adjuvant and injected intradermally, said animals receiving booster injections with p20 polypeptide or degraded p20 polypeptide and bled thereafter.

8. A method according to claim 7, wherein said Freund's adjuvant is supplemented with Mycobacterium tuberculosis cells.

9. A method of detecting p21 ras gene-expressed proteins comprising obtaining anti-p20 antibodies according to the method of claim 7 and detecting said p21 ras gene-expressed proteins with said anti-p20 antibodies by immunoprecipitation.

10. A method of detecting p21 ras gene-expressed proteins comprising obtaining anti-p20 antibodies according to the method of claim 7 and detecting said p21 ras gene-expressed proteins with said anti-p20 antibodies by immunoblotting.

11. A method of detecting p21 ras gene-expressed proteins comprising obtaining anti-p20 antibodies according to the method of claim 7 and detecting said p21 ras gene-expressed proteins with said anti-p20 antibodies by immunofluorescence.

* * * * *